US012758597B2

(12) United States Patent
Saiz et al.

(10) Patent No.: US 12,758,597 B2
(45) Date of Patent: Oct. 13, 2026

(54) COMBINATION OF LACTOBACILLUS STRAINS AND USE THEREOF IN ANIMAL HEALTH

(71) Applicants: LESAFFRE ET COMPAGNIE, Paris (FR); UNIVERSITE DE LILLE, Lille (FR)

(72) Inventors: Nuria Vieco Saiz, Madrid (ES); Ruth Raspoet, Erembodgem (BE); Eric Auclair, Avelin (FR); Djamel Drider, Roubaix (FR); Frédérique Gancel, Hellemes (FR)

(73) Assignees: LESAFFRE et COMPAGNIE, Paris (FR); UNIVERSITE DE LILLE, Lille (FR)

( * ) Notice: Subject to any disclaimer, the term of this patent is extended or adjusted under 35 U.S.C. 154(b) by 513 days.

(21) Appl. No.: 18/016,622

(22) PCT Filed: Jul. 19, 2021

(86) PCT No.: PCT/FR2021/051348
§ 371 (c)(1),
(2) Date: Jan. 17, 2023

(87) PCT Pub. No.: WO2022/018373
PCT Pub. Date: Jan. 27, 2022

(65) Prior Publication Data
US 2023/0285476 A1 Sep. 14, 2023

(30) Foreign Application Priority Data
Jul. 20, 2020 (FR) ...................................... 2007632

(51) Int. Cl.
*A61K 35/747* (2015.01)
*A61P 1/00* (2006.01)
(Continued)

(52) U.S. Cl.
CPC .............. *A61K 35/747* (2013.01); *A61P 1/00* (2018.01); *A61P 31/04* (2018.01); *C12N 1/205* (2021.05); *C12R 2001/225* (2021.05)

(58) Field of Classification Search
CPC .......... A61K 35/747; A61P 31/04; A61P 1/00; C12N 1/205; C12R 2001/225
(Continued)

(56) References Cited

U.S. PATENT DOCUMENTS

2014/0328932 A1* 11/2014 Mogna ................ A61K 35/744 424/490

FOREIGN PATENT DOCUMENTS

CN 105861399 A 8/2016
EP 2287286 A1 2/2011
(Continued)

OTHER PUBLICATIONS

Pei-Shan Hsieh, et al.,—Lactobacillus salivarius AP-32 and Lactobacillus reuteri GL-104 decrease glycemic levels and attenuate diabetes-mediated liver and kidney injury in db/db mice: BMJ Open Diabetes Research & Care 2020 (Year: 2020).*
(Continued)

*Primary Examiner* — Robert B Mondesi
(74) *Attorney, Agent, or Firm* — MARSHALL, GERSTEIN & BORUN LLP

(57) ABSTRACT

The present invention relates to a mixture of microorganisms comprising a *Lactobacillus reuteri* strain and a *Lactobacillus salivarius* strain, and to the use thereof for preparing an animal additive or feed product and for preventing or treating necrotic enteritis.

19 Claims, 1 Drawing Sheet

(51) Int. Cl.
*A61P 31/04* (2006.01)
*C12N 1/205* (2026.01)
*C12R 1/225* (2006.01)

(58) Field of Classification Search
USPC ........................................................ 424/93.45
See application file for complete search history.

(56) References Cited

FOREIGN PATENT DOCUMENTS

WO WO-2006/133472 A1 12/2006
WO WO-2016/170280 A1 10/2016

OTHER PUBLICATIONS

Hsieh P., et al.,—Lactobacillus salivarius AP-32 and Lactobacillus reuteri GL-104 decrease glycemic levels and attenuate diabetes-mediated liver and kidney injury in db/db mice: BMJ Open Diabetes Research & Care 2020;8:e001028. https://doi.org/ 10.1136/bmjdrc-2019-001028 (Year: 2020).*

Ren Hao et al., "Synergistic effects of probiotics and phytobiotics on the intestinal microbiota in young broiler chicken", Microorganisms, vol. 7, No. 12, p. 684 (2019).

International Search Report and Written Opinion for PCT/FR2021/051348 dated Nov. 22, 2021.

Klose et al., "In vitro antagonistic activities of animal intestinal strains against swine-associated pathogens", Veterinary Microbiology, Elsevier BV, NL, vol. 144, No. 3-4, pp. 515-521 (2010).

Prescott et al., "The use of Bacitracin in the prevention and treatment of experimentally-induced necrotic enteritis in the Chicken", Can. Vet. J., vol. 19, pp. 181-183 (1978).

Ghareeb et al., Evaluating the efficacy of an avian-specific probiotic to reduce the colonization of Campylobacter jejuni in broiler chickens, Poultry Sci., 91: 1825-1832 (Jan. 2012).

* cited by examiner

COMBINATION OF LACTOBACILLUS STRAINS AND USE THEREOF IN ANIMAL HEALTH

CROSS REFERENCE TO RELATED APPLICATIONS

This application is a U.S. national stage of International Patent Application No. PCT/FR2021/051348, filed Jul. 19, 2021, which claims the benefit of French Patent Application No. 2007632, filed Jul. 20, 2020, the entire contents of each of which are fully incorporated herein by reference.

FIELD OF THE INVENTION

The present invention describes a combination of lactobacilli (or lactic bacteria), namely a *Lactobacillus reuteri* strain and a *Lactobacillus salivarius* strain, and the use thereof for preventing and/or treating necrotic enteritis in animals, in particular chickens.

PRIOR ART

In 2017, the world meat production increased by 1.25% reaching 323 million metric tons (MT) and it is expected to grow further by close to 15% by 2027 (Organization for Economic Cooperation and Development (OECD)/*Food and Agriculture Organization* (FAO), 2018). The growth of the demand for meat products is mainly due to demographic growth, urbanization and the increase in incomes in developing countries.

The production of poultry meat represents the main sector in the industry of meat products.

"Poultry" is understood to mean domestic birds belonging to the gallinaceae or the palmipeds which are raised for their meat, their eggs and their feathers. The term "poultry" covers a broad range of birds from indigenous and commercial hen breeds to muscovy ducks, mallard ducks, turkeys, guinea fowl, geese, quail, pigeons, ostriches or pheasants. The most consumed poultry meat is chicken meat.

Poultry meat is mainly produced in the context of large-scale intensive animal farming. The world poultry industry has become a sector that generates large profits, the success of which is intimately connected with the health of the animals and more precisely with their healthy gastrointestinal tract which ensures effective absorption of the feeds given to the poultry.

In fact, avian diseases, that is to say diseases that affect birds, can generate major financial losses due to the high mortality rate and the low feed efficiency. These infections can be of bacterial, fungal, viral or parasitic origin. Thus, the most common bacterial infections in birds are infections due to *Escherichia coli, Salmonella* spp, *Clostridium perfringens, Pasteurella multocida, Staphylococcus aureus, Mycobacterium avium, Mycoplasma gallisepticum, Mycoplasma synoviae, Mycoplasma meleagridis, Mycoplasma iowae, Clostridium sordellii* or else *Clostridium septicum*. These strains cause various diseases such as chronic respiratory disease in poultry, avian cholera, gangrenous dermatitis, necrotic enteritis or avian tuberculosis.

*Escherichia coli* and the bacteria of the genus *Clostridium* are among the most important agents of enteric diseases in poultry.

The bacteria of the genus *Clostridium* (or clostridia) are endospore-producing gram-positive anaerobic bacilli. They are ubiquitous, that is to say they can be found in the environment and in the gastrointestinal tract of animals. It should be noted that these bacteria are for the most part nonpathogenic. Many of these bacteria are widely used in industrial fermentation, for example, in the synthesis of chemical compounds such as acetate, butyrate, lactate, ethanol, carbon dioxide or solvents.

Nonetheless, certain bacteria of the genus *Clostridium* (C.) are known for their pathogenic power. They are notably *C. botulinum, C. tetani, C. difficile, C. perfringens, C. novyi*, and *C. septicum*. The clostridia cause several disorders including ulcerous enteritis caused by *C. colinum* or also necrotic enteritis caused by *C. perfringens.*

Necrotic enteritis or necrotizing enteritis is a disease that affects animal farms in all the poultry regions of the world. This pathology is more common in broiler chickens, but laying hens and turkeys can also be affected.

The capacity of *C. perfringens* to cause this pathology depends on the production of certain extracellular toxins and enzymes causing a degradation of the intestinal cells, such as lecithinases or necrotizing toxins.

For example, *C. perfringens* produces and secretes alpha-toxin ($\alpha$-toxin), a lecithinase causing hemolysis and tissue necrosis, or also $\beta$-toxin (or Necrotic enteritis toxin B-like or NetB) causing the formation of endospores in the membrane of intestinal cells.

The bacterium *C. perfringens* is naturally present in the intestine. As an opportunistic bacterium, it requires the intestinal equilibrium to be compromised in order to colonize, proliferate and express its toxins and thus cause necrotic enteritis. Studies have notably shown that simple infection with *C. perfringens* alone is not sufficient to induce the pathology. The triggering of necrotic enteritis requires the presence of conditions referred to as predisposing factors, such as coccidiosis, a disease caused by the parasite *Eimeria* spp, feed or also immunosuppression or stress of the animals.

Necrotic enteritis negatively affects the feed conversion rate in farmed animals, that is to say that the animals must consume more feed to have the same weight gain. This type of necrotic enteritis is problematic because it has a negative impact on the productivity and the profitability, resulting in animals of reduced size and weight.

The most common signs allowing the detection of necrotic enteritis are the appearance of somnolence in animals, lack of tone and appetite, diarrhea, dehydration or also lack of appetite. The chickens generally die within 1 to 2 hours after the appearance of the symptoms. The mortality rates associated with necrotic enteritis are generally between 2 and 10% but sometimes can reach 50%. The disorder is characterized by the sudden increase in the mortality of the livestock, the birds generally dying without precursor signs.

Necrotic enteritis is thus responsible every year for colossal economic losses in the world, evaluated at more than 6 billion dollars in 2015. These losses are due to the costs of the disease control measures and to the decrease of production in terms of weight and mortality of the animals in animals farms.

This is why necrotic enteritis prevention and/or treatment strategies in farmed animals are necessary.

One of the ways to combat necrotic enteritis is prevention since, as mentioned above, after infection, the development of the disease is a very rapid and the mortality is high.

The administration of antibiotics at low concentration, that is to say the administration of growth promoters (or AGP for Antibiotics Growth Promoters) such as avoparcin, bacitracin and virginiamycin, is very effective in the prevention and control of necrotic enteritis. These AGP promote the growth of the animals and improve the efficiency of the feed conversion. It should be noted that these compounds are also used in human medicine, at higher concentrations.

However, the abuse of these antibiotics, notably in human and veterinary medicine, caused a selective pressure which accelerated the evolution and the propagation of resistant bacteria. Consequently, their use is prohibited as AGP and it is retained only in human medicine, notably in Europe.

After the restrictions on the use of AGP, alternatives for preventing and/or treating necrotic enteritis were developed, such as the use of NetB toxoids, or vaccination with *Eimeria*, a unicellular parasite, in order to reduce the prevalence of coccidiosis which is known to be an important predisposing factor for necrotic enteritis.

However, in order to overcome the increase in mortality and morbidity rates associated with the prohibition of antibiotics in animal feed, there remains an obvious need for developing alternatives which have performances similar to those obtained with antibiotics in the prevention and/or treatment of necrotic enteritis.

Due to their properties, lactic bacteria are widely used in the agro-food industry as biological food preservative or in industrial animal farms for the prevention of infectious and zoonotic diseases. These bacteria are also used to improve the performance of animal farms by the production of digestive enzymes, volatile fatty acids and/or vitamins, which participate in the increase of the digestibility of nutrients and in the improvement of the feed conversion rate. These lactic bacteria are notably found under the name of probiotics.

Thus, an alternative to the use of antibiotics or AGP consists in giving the animals feed additives or products, in particular probiotics.

In general, probiotics are defined as living microorganisms which confer a benefit for the health of the host, when consumed at sufficient concentrations. They can interact with the host to improve the immunity, the intestinal homeostasis, to stimulate the metabolism or also to reduce the risk of infection by opportunistic pathogens.

Certain probiotic bacteria interfere with, and even annihilate, the pathogenicity of the pathology-causing microbial agents, for example, by eliminating or inhibiting the growth of the pathogenic bacteria in the intestinal lumen. Some of these probiotic bacteria produce antibacterial substances capable of competing with the pathogens for the nutrients, the growth factors and the binding sites of the intestinal epithelium. They can also perform immunological functions by modulating the immune response of the host, thus enabling the host to better combat the infections.

Most of the bacterial probiotics belong to the lactic bacteria. One of the main characteristics of this group of bacteria is their ability to produce lactic acid in a strain-dependent manner by homo- or heterofermentative fermentation of glucose.

The lactic bacteria belong to phylum of the *Firmicutes* of the class of the *Bacilli* and the order of the *Lactobacilluses*. The taxon referred to as lactic bacteria groups together gram-positive, nonsporulating, facultative anaerobic or aerobic cocci, bacilli or coccobacilli having a G+C percentage of less than 50%. These bacteria are acidophiles with an optimal growth pH between 3.5 and 6.5. Most of the strains have nutritional requirements and require rich media to develop. This group includes 10 genera, the best-known being *Lactobacillus, Pediococcus, Lactococcus, Enterococcus, Streptococcus, Leuconostoc* and Carnobacterium.

Among the lactic bacteria, the most represented genus is that of *Lactobacillus* (Lb.) with more than 253 species described to date (http://www.bacterio.net/*lactobacillus*.html).

The lactobacilli are widely used in the production of probiotics, notably because of their ability to survive under the extreme conditions encountered in the gastrointestinal tract, their good ability to adhere to the intestinal cells, which makes it possible to increase the retention of the probiotics in the intestine, properties of eliminating or inhibiting the growth of pathogenic bacteria in the intestinal lumen.

The document EP 2 287 286 notably describes that isolates of *Lactobacillus* (*Lb. sakei* or *Lb. reuteri*) possess anti-inflammatory and probiotic properties.

The document CN 105861399 also describes the use of a specific *Lb. plantarum* strain for preventing necrotic enteritis in farmed chickens by inhibition of the growth of *C. perfringens*.

The document WO2006/133472 describes a complex mixture of 5 *C. perfringens*-inhibiting microorganisms, consisting of *E. faecium* DSM 16211, *L. reuteri* DSM 16350, *L. salivarius* DSM 16351, *P. acidilactici* DSM 16210 and *B. animalis* DSM 16284. This document specifies that these specific strains of *L. reuteri* and *L. salivarius* are more effective in inhibiting *E. coli* than *C. perfringens*.

The document WO2016/170280 recommends the use of *Bacteroides* thetaiotaomicron, possibly combined with *L. reuteri* and/or *L. salivarius*, notably for treating enteritis. KLOSE et al. (Veterinary Microbiology, 2010, 144 (3-4): 515-21) evaluated the antagonistic activity of different intestinal bacteria, including *L. reuteri* and *L. salivarius*, with respect to *C. perfringens*, reporting a great heterogeneity between the species.

REN et al. (Microorganisms, 2019, 7 (12): 684) reported a synergistic effect between probiotic (*L. agilis* or *L. salivarius*) and phytobiotic on the intestinal microbiota of young farmed chickens.

However, there is an obvious need to develop new effective solutions, having a simple formula and containing a minimum of active substances, in view of combatting *C. perfringens* which is responsible for necrotic enteritis of broiler chickens, for health and economic reasons.

DISCLOSURE OF THE INVENTION

Definitions

The definitions below correspond to the meaning generally used in the context of the invention and should be taken into consideration unless another definition is explicitly indicated.

In the sense of the invention, the articles "a" and "an" are used to refer to one or more (for example, at least one) units of the grammatical object of the article. For example, "an element" designates at least one element, that is to say one element or more.

The terms "about" or "approximately" used in reference to a measurable value such as a quantity, a duration, and other similar values must be understood to encompass measurement uncertainties of +20% or +10%, preferably +5%, even more preferably +1% and particularly preferably ±0.1% of the specified value.

Intervals: throughout the present description, the different features of the invention can be presented in the form of an interval of values. It should be understood that the description of values in the form of an interval is intended only to make the reading simpler and should not be interpreted as a strict limitation of the scope of the invention. Consequently, the description of an interval of values should be considered to specifically disclose all the possible intermediate intervals as well as each of the values within this interval. For example, the description of an interval from 1 to 6 should be considered to specifically describe each of the intervals that it includes, such as the intervals from 1 to 3, from 1 to 4, from 1 to 5, from 2 to 4, from 2 to 6, from 3 to 6, etc., as well as each of the values in this interval, for example, 1; 2; 2.7; 3; 4; 5; 5.3 and 6. This definition is valid independently of the range of the interval.

In the context of the invention, the term "isolated" should be understood to be synonymous with removed or extracted from its environment or natural state. For example, an isolated bacterial strain or peptide is a bacterial strain or peptide extracted from the natural environment in which it is usually found, whether this is a plant or a living animal, for example. Thus, a bacterial strain or a peptide which is naturally present in a living animal is not an isolated bacterial strain or peptide in the sense of the invention, while the same bacterial strain or peptide, partially or completely separated from the other elements present in its natural context is itself "isolated" in the sense of the invention. An isolated bacterial strain or peptide can exist in a substantially purified form or in a non-native environment such as, for example, a host cell.

Surprisingly, the Applicant identified a specific novel combination of lactic bacteria which is useful for combating necrotic enteritis, in particular in farmed animals such as chickens.

Thus, and according to a first aspect, the present invention relates to a mixture of microorganisms comprising a *Lactobacillus reuteri* strain and a *Lactobacillus salivarius* strain.

In the sense of the invention, "mixture" is used to designate the combination of at least 2 different species of microorganisms, advantageously at least 2 distinct bacterial strains, even more advantageously at least 2 distinct strains of lactic bacteria (lactobacilli or *Lactobacillus*)

Thus, a mixture of microorganisms according to the invention can comprise one or more Lb. *reuteri* strains and one or more *Lb. salivarius* strains, and possibly other microorganisms, notably other bacteria.

According to another aspect, the present invention relates to a mixture of lactic bacteria consisting of at least one *Lb. reuteri* strain and of at least one *Lb. salivarius* strain. According to a particular embodiment, the mixture of lactic bacteria consists of one *Lb. reuteri* strain and of at least one *Lb. salivarius* strain, possibly of two *Lb. salivarius* strains. According to another embodiment, the mixture of lactic bacteria consists of one *Lb. reuteri* strain and of one *Lb. salivarius* strain.

As shown in the present application, the specific mixture according to the invention is capable of reducing or inhibiting the growth and/or the activity of the bacterium *C. perfringens.*

In the sense of the invention, "growth of the bacterium *C. perfringens*" is used to designate a set of mechanisms leading to an increase of the dry biomass of bacteria. This involves the growth of the bacterial cell in size, weight and/or volume but also the growth of a population by cell division.

In the sense of the invention, "activity of the bacterium *C. perfringens*" is used to designate the pathogenic activity or also the toxicogenic activity of this bacterium. This notably involves the production or secretion of toxins such as NetB and α-toxin, or of enzymes. This can also involve the ability of *C. perfringens* to adhere to the gastrointestinal tract or even colonize it.

Advantageously, the mixture according to the invention enables a reduction or even an inhibition of the production and/or of the secretion of the toxins NetB and α-toxin.

According to a particular embodiment, the mixture according to the invention comprises the *Lb. reuteri* strain deposited pursuant to the Budapest Treaty at the CNCM (Collection Nationale de Cultures de Microorganismes [National Collection of Cultures of Microorganisms], Institut Pasteur [Pasteur Institute], 25 rue du Docteur Roux, 75724 Paris Cedex 15) under number 1-5500 on Mar. 4, 2020.

According to another particular embodiment, the mixture according to the invention comprises the *Lb. salivarius* strain deposited pursuant to the Budapest Treaty at the CNCM (Collection Nationale de Cultures de9 Microorganismes, Institut Pasteur, 25 rue du Docteur Roux, 75724 Paris Cedex 15) under number 1-5501 on Mar. 4, 2020 and/or the Lb. *salivarius* strain deposited pursuant to the Budapest Treaty at the CNCM under number I-5502 on Mar. 4, 2020.

According to a specific embodiment, the mixture of microorganisms according to the invention comprises or consists of:

- a *Lactobacillus reuteri* strain and a *Lactobacillus salivarius* strain, said *Lb. reuteri* strain being the strain deposited at the CNCM (Collection Nationale de Cultures de Microorganismes, Institut Pasteur, 25 rue du Docteur Roux, 75724 Paris Cedex 15) under number I-5500 on Mar. 4, 2020; or
- a *Lactobacillus reuteri* strain and a *Lactobacillus salivarius* strain, said *L. salivarius* strain being the strain deposited at the CNCM (Collection Nationale de Cultures de Microorganismes, Institut Pasteur, 25 rue du Docteur Roux, 75724 Paris Cedex 15) under number I-5501 on Mar. 4, 2020; and/or the strain deposited at the CNCM (Collection Nationale de Cultures de Microorganismes, Institut Pasteur, 25 rue du Docteur Roux, 75724 Paris Cedex 15) under number I-5502 on Mar. 4, 2020; or
- the *Lb. reuteri* strain deposited at the CNCM (Collection Nationale de Cultures de Microorganismes, Institut Pasteur, 25 rue du Docteur Roux, 75724 Paris Cedex 15) under number I-5500 on Mar. 4, 2020 and the *Lb. salivarius* strain deposited at the CNCM (Collection Nationale de Cultures de Microorganismes, Institut Pasteur, 25 rue du Docteur Roux, 75724 Paris Cedex 15) under number I-5501 on Mar. 4, 2020 and/or the *Lb. salivarius* strain deposited at the CNCM (Collection Nationale de Cultures de Microorganismes, Institut Pasteur, 25 rue du Docteur Roux, 75724 Paris Cedex 15) under number I-5502 on Mar. 4, 2020.

According to different embodiments, the mixture according to the invention comprises or consists of:

- the *Lb. reuteri* strain deposited at the CNCM (Collection Nationale de Cultures de Microorganismes, Institut Pasteur, 25 rue du Docteur Roux, 75724 Paris Cedex 15) under number I-5500 on Mar. 4, 2020 and the *Lb. salivarius* strain deposited at the CNCM (Collection Nationale de Cultures de Microorganismes, Institut Pasteur, 25 rue du Docteur Roux, 75724 Paris Cedex 15) under number I-5501 on Mar. 4, 2020; or
- the *Lb. reuteri* strain deposited at the CNCM (Collection Nationale de Cultures de Microorganismes, Institut Pasteur, 25 rue du Docteur Roux, 75724 Paris Cedex 15) under number I-5500 on Mar. 4, 2020 and the *Lb. salivarius* strain deposited at the CNCM (Collection Nationale de Cultures de Microorganismes, Institut Pasteur, 25 rue du Docteur Roux, 75724 Paris Cedex 15) under number I-5502 on Mar. 4, 2020; or the *Lb. reuteri* strain deposited at the CNCM (Collection Nationale de Cultures de Microorganismes, Institut Pasteur, 25 rue du Docteur Roux, 75724 Paris Cedex 15) under number I-5500 on Mar. 4, 2020, the *Lb. salivarius* strain deposited at the CNCM (Collection Nationale de Cultures de Microorganismes, Institut Pasteur, 25 rue du Docteur Roux, 75724 Paris Cedex 15) under number I-5501 on Mar. 4, 2020 and the *Lb. salivarius* strain deposited at the CNCM (Collection Nationale de Cultures de Microorganismes, Institut Pasteur, 25 rue du Docteur Roux, 75724 Paris Cedex 15) under number I-5502 on Mar. 4, 2020.

According to a particular embodiment, the mixture contains other microorganisms, advantageously other probiotics. Preferably, the mixture contains other microorganisms selected from: bacteria of the genus *Lactobacillus*, bacteria of the genus *Bifidobacterium*, bacteria of the genus *Streptococcus*, bacteria of the genus *Enterococcus*, bacteria of the genus *Pediococcus*, bacteria of the genus *Bacillus*, yeasts, and combinations thereof.

Preferably, the *Lactobacillus* bacterium is selected from the group consisting of: Lb. *acidophilus, Lb. lactis, Lb. helveticus, Lb. brevis, Lb. casei, Lb. plantarum, Lb. salivarius*, advantageously another *Lb. salivarius* strain, *Lb. reuteri*, advantageously another *Lb. reuteri* strain, *Lb. bifidus, Lb. bulgaricus*, Lb. caucasicus, *Lb. rhamnosus*, Lb. gasseri, Lb. sakei, *Lb. fermentum*, strain, and combinations thereof.

Preferably, the *Bifidobacterium* bacterium is selected from the group consisting of: *B. bifidum, B. longum, B. infantis, B. breve, B. adolescentis, B. animalis, B. lactis*, and combinations thereof.

Preferably, the *Streptococcus* bacterium is selected from the group consisting of: *S. thermophilus, S. lactis, S. cremoris*, S. diacetylcatis, and combinations thereof.

Preferably, the *Enterococcus* bacterium is selected from the group consisting of: *E. faecium, E. faecalis*, and combinations thereof.

Preferably, the *Pediococcus* bacterium is *P. acidilactici.*

Preferably, the *Bacillus* bacterium is selected from the group consisting of: *B. subtilis, B. velezensis, B. licheniformis, B. coagulans, B. pumilus*, and combinations thereof.

Preferably, the yeast is selected from the group consisting of: *Candida Kefyr, Saccharomyces florentinus, Saccharomyces cerevisiae, Saccharomyces cerevisiae* var. *boulardii*, and combinations thereof.

According to another aspect, the present invention relates to a composition comprising a mixture of microorganisms, as defined above.

Furthermore, the composition according to the invention can comprise the usual adjuvants or excipients used in the field in question, such as hydrophilic or lipophilic thickeners or gelling agents, palatants, hydrophilic or lipophilic additives, preservatives, antioxidants, diluents, vitamins, minerals, suspension agents, cellulose derivatives, absorbents, cryoprotective agents or also dyes.

Naturally, a person skilled in the art will make sure to select this adjuvant or excipient or these adjuvants or excipients and adjust the quantity thereof in such a manner that the advantageous properties of the composition according to the invention are not altered or not substantially altered by the addition considered.

According to an embodiment, the composition according to the invention comprises nutritional substances that can be used as support, and/or prebiotic substances advantageously selected from fructooligosaccharides, inulins, isomaltooligosaccharides, lactitol, lactosucrose, lactulose, pyrodextrins, soybean oligosaccharides, transgalactooligosaccharides, xylooligosaccharides, vitamins, in particular vitamin E.

According to another embodiment, the composition according to the invention comprises at least one compound selected from the following group: zeolites, calcium carbonate, calcium sulfate, magnesium carbonate, talc, trehalose, chitosan, shellac, albumin, starch, powdered skim milk, whey, powdered whey, maltodextrins, lactose, inulin, dextroses, celluloses, clays including sepiolite, yeast and cereal derivatives, vegetable oils or a solvent selected from water or a physiological saline solution.

According to a particular embodiment, the composition according to the invention comprises a coating material advantageously selected from maltodextrins, guar seed meal, gum arabic, alginates, modified starch and starch derivatives, dextrins, cellulose derivatives such as cellulose ester and cellulose ether, proteins such as gelatin, albumin, casein, gluten, gum arabic, tragaganth gum, lipids such as waxes, paraffin, stearic acid, mono- and diglycerides.

The mixture or the composition according to the invention can be in the form of a powder, a capsule, a spray, a solution, an emulsion, a suspension or a dispersion.

Advantageously, the mixture or the composition according to the invention is in dry or liquid form, notably in lyophilized, dried, pressed, liquid or deep-frozen form, advantageously in lyophilized form.

According to a preferred embodiment, the mixture or the composition according to the invention is intended to be administered orally. For this purpose, the mixture or the composition can be in different suitable galenic forms, for example, in the form of a lyophilizate to be poured and solubilized in the drinking water, a liquid to be poured on the feed or into the drinking water, tablets, powder packaged in capsules or any other appropriate form. Advantageously, it is a powder or lyophilizate to be poured and solubilized in the drinking water of the animals.

According to a particular embodiment, the mixture or the composition according to the invention contains lactobacilli according to the invention at a final concentration between $10^5$ and $10^9$ CFU (Colony Forming Unit)/mL of the mixture or of the composition according to the invention, advantageously between $10^6$ and $10^8$ CFU/mL, for example, at a final concentration of $10^7$ CFU/mL.

This concentration can be understood to be the concentration of each microorganism, advantageously bacterium, even more advantageously *lactobacillus*, present in the mixture or the composition, advantageously in the drinking water of the animals. Preferably, it is the concentration of all the microorganisms, advantageously bacteria, even more advantageously lactobacilli, present in the mixture or the composition. Thus and as an example, for a final concentration of lactobacilli of $10^7$ CFU/mL, a mixture according to the invention can comprise or consist of a *Lb. reuteri* strain and a *Lb. salivarius* strain at a concentration of $0.5\times10^7$ CFU/mL each.

According to another aspect, the invention relates to the use of a mixture or of a composition according to the invention as animal additive or feed product.

In the sense of the invention "additive or feed product" is used to designate a composition which is intended to supplement the traditional feed diet and including nutrients or other substances having a nutritional or physiological effect. As already stated, it can be an additive for drinking water or for feeds such as, for example, cereals and/or pulses such as soybeans. By convention, the term "drink" is used for ingested products in liquid form and the term "feed" is used for ingested products in solid form.

The mixture or the composition according to the invention can be extemporaneously added to the drink or to the feeds, or it can notably be introduced into the feeds at the time of their production, for example, by mixing or coating.

According to a particular embodiment, the mixture or the composition according to the invention is added to the drink or to the feeds in such a way that the lactobacilli represent from $10^8$ to $10^{14}$ CFU/kg of the drink or the feed, advantageously from $10^{10}$ to $10^{12}$ CFU/kg.

According to another aspect, the invention relates to the use of a mixture or a composition as described above, as well as to drink and feeds containing them, for combating necrotic enteritis in animals, that is to say for preventing and/or treating this pathology.

In a known manner and as described in the examples, the efficacy against necrotic enteritis can be evaluated by determining an intestinal lesion score of the animals:

- the score 0 corresponds to a healthy intestine;
- the score 1 corresponds to a thin and friable intestine;
- the score 2 corresponds to a thin and friable intestine with the appearance of necrotic spots of small size; and
- the score 3 corresponds to an intestine having large lesions visible through the external wall of the intestinal tract.

The prevention and/or the treatment of necrotic enteritis can also be evaluated by monitoring the weight of the animals. As mentioned above, the intestinal lesions decrease the conversion of the feeds, which induces a weight loss of the animals.

According to a preferred embodiment, the animal to which the present invention relates is a poultry animal, advantageously a chicken, preferably a broiler chicken (or farmed chicken).

As already stated and preferably, the mixture or the composition according to the invention, possibly incorporated in the drink or in the feeds, is administered or ingested orally.

The ingestion can be systematic for all the animals from birth on or it can be decided on at the appearance of symptoms or deaths in the animal farm. Advantageously, the treatment is carried out preventively, that is to say before the appearance of any symptom, from the birth of the animals on or after a few days. Even more advantageously, the treatment is continued until the death of the animals, which occurs generally after 40 days for poultry.

Moreover, the ingestion can take place once daily, or even every time drink or feed is ingested, or it can be spaced over several days. Advantageously, the ingestion is daily.

A preferred dosage corresponds to a daily administration, in the form of a feed supplement at a concentration of $10^7$ CFU/mL (equivalent to $10^7$ CFU/g), throughout the entire life of the animal.

According to another aspect, the invention relates to lactobacilli strains listed below, which are of interest because of their inhibitory activity on the growth and/or the activity of *Clostridium perfringens:*

- the *Lb. reuteri* strain deposited at the CNCM (Collection Nationale de Cultures de Microorganismes, Institut Pasteur, 25 rue du Docteur Roux, 75724 Paris Cedex 15) under number I-5500 on Mar. 4, 2020;
- the *Lb. salivarius* strain deposited at the CNCM (Collection Nationale de Cultures de Microorganismes, Institut Pasteur, 25 rue du Docteur Roux, 75724 Paris Cedex 15) under number I-5501 on Mar. 4, 2020;
- the *Lb. salivarius* strain deposited at the CNCM (Collection Nationale de Cultures de Microorganismes, Institut Pasteur, 25 rue du Docteur Roux, 75724 Paris Cedex 15) under number I-5502 on Mar. 4, 2020.

EMBODIMENT EXAMPLES OF THE INVENTION

The way the invention can be carried out and the advantages derived therefrom will become apparent from the following embodiment examples given for information and in a nonlimiting manner, in support of the appended figure.

Figure 1:
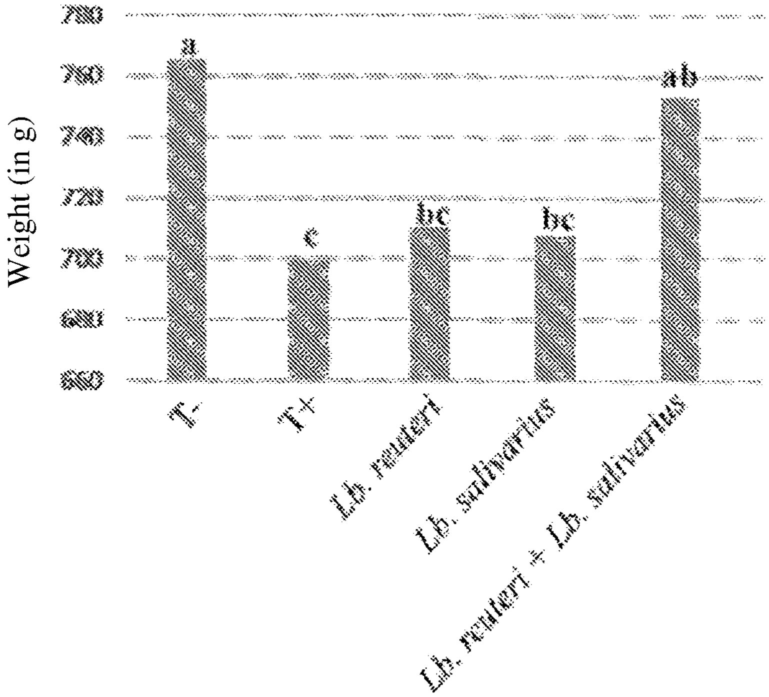
FIG. 1 represents the efficiency of the bacterial mixture according to the invention in terms of weight of the chickens. The letters (a, b, c) indicate statistically significant differences.

Demonstration of the Effect of the Bacterial Mixture According to the Invention Against Necrotic Enteritis Experiments were carried out using the *Lb. reuteri* strain deposited at the CNCM (Collection Nationale de Cultures de Microorganismes, Institut Pasteur, 25 rue du Docteur Roux, 75724 Paris Cedex 15) under number I-5500 on Mar. 4, 2020 and the *Lb. salivarius* strain deposited at the CNCM (Collection Nationale de Cultures de Microorganismes, Institut Pasteur, 25 rue du Docteur Roux, 75724 Paris Cedex 15) under number I-5501 on Mar. 4, 2020.

The *C. perfringens* strain used in the example is a *C. perfringens* strain isolated from chicken suffering from necrotic enteritis.

1/Material and Methods:

The ability of the combination of *Lb. reuteri* and *Lb. salivarius* according to the invention to prevent necrotic enteritis was evaluated in vivo on broiler chickens from a cross of the Cobb 500 (female) breed and Hubbard M99 (male) breed.

The in vivo experiments took place over 17 days on 150 chickens (30 for each experimental condition). The test was started on the day of hatching. During the tests, the lactobacilli were administered alone (*Lb. reuteri, Lb. salivarius*) or in combination (*Lb. reuteri+Lb. salivarius*) by force feeding once daily, on days 1 and 2, and then from day 10 to day 13.

1-1/Environment of the Chickens and Diet

The chickens were raised in cages providing an average surface area of 432 $cm^2$ per chicken. The cages were placed at several levels in an air-conditioned room kept at ambient temperature throughout the study and authorized for tests with a biological risk of level 2. The lighting was provided 24/24 hours for the entire duration of the study. The birds received water and feed ad libitum, that is to say they were fed to satiety.

The feed of the first 9 days is corn- and soybean-based. After day 10, the growth diet included wheat (Tables 1 and 2). The two diets are administered in puree form.

TABLE 1

| represents the composition of the diets by ingredients (g/100 g) | | |
|---|---|---|
| | Starting diet (0-9 days) | Growth diet (10-17 days) |
| Corn | 60.83 | 34.87 |
| Soybean meal (48%) | 33.91 | 28.14 |
| Wheat | — | 20.00 |
| Dried grains for distillation | — | 10.00 |
| Mixture of vegetable fats | 1.17 | 3.06 |
| Limestone | 1.47 | 1.45 |
| Monocalcium phosphate | 1.54 | 1.44 |
| NaCl | 0.44 | 0.28 |
| L-Lysine HCl | 0.15 | 0.26 |
| DL-Methionine | 0.21 | 0.21 |
| L-Threonine | 0.06 | 0.08 |
| Vitamin premix | 0.18 | 0.18 |
| Mineral premix | 0.05 | 0.05 |

TABLE 2

| represents the approximative composition of the diets (g/100 g) | | |
|---|---|---|
| | Starting diet (0-9 days) | Growth diet (10-17 days) |
| Dry matter | 87.98 | 88.93 |
| Proteins | 22.00 | 22.00 |
| Fat | 3.63 | 5.87 |
| Fiber | 2.17 | 2.89 |
| Ash | 5.45 | 5.54 |
| Lysine | 1.3 | 1.3 |
| Calcium | 0.88 | 0.88 |
| Phosphorous | 0.70 | 0.71 |
| Apparent metabolizable energy value (kcal/kg) | 3,000.00 | 3,000.00 |

1-2/Vaccination

Except for the unchallenged group (which did not receive any administration of *C. perfringens*), the chickens were vaccinated on day 1 with Advent@9X. This vaccine contains live *Eimeria acervulina, E. maxima* and *E. tenell* oocysts, gentamycin and amphotericin B as preservatives. The objective is to help prevent avian coccidiosis generated by these pathogens. On the 9$^{th}$ day, the chickens were vaccinated intraocularly against avian infectious bursitis with Intervet, Bursal Vac-G603 which is a vaccine containing live viruses.

1-3/Treatment of the Different Lots

Five different treatments were tested. Each treatment was repeated six times, and each replica contains 5 chickens.

These treatments are recapitulated below:

T−: Control group not supplemented with lactobacilli and unchallenged with *C. perfringens;*

T+: Positive control group, not supplemented with lactobacilli, and challenged with *C. perfringens;*

*Lb. reuteri*: supplemented with *Lb. reuteri* and challenged with *C. perfringens;*

*Lb. salivarius*: supplemented with *Lb. salivarius* and challenged with *C. perfringens;*

*Lb. reuteri+Lb. salivarius*: supplemented with a mixture of *Lb. reuteri* and *Lb. salivarius* and challenged with *C. perfringens.*

1-4/Administration of *C. perfringens*

The wild strain of *C. perfringens* was cultured in thioglycolate broth overnight at 37° C. *C. perfringens* was then administered at a concentration of $10^7$ CFU/mL at an oral force-feeding dose of 3 mL administered in sterile thioglycolate, using a 20-mL syringe and a gauge 20 metering needle, from the 14th to the 16th day of age. After the administration, the birds were immobilized by hand for 5 to 10 s in order to confirm the delivery of the appropriate dose and the absence of stress. 1-5/Administration of the lactic bacteria The lactic bacteria strains were cultured in MRS (Man-Rogosa-Sharpe) broth at 37° C. overnight. On the 1$^{st}$ and 2$^{nd}$ days of age, 250 to 500 μL of suspension of *Lactobacillus* at $10^7$ CFU/mL (alone or at a final concentration of the mixture of the 2 *Lb. reuteri* and *Lb. salivarius* strains, that is to say at $0.5\times10^7$ CFU/mL each concerning the mixture) were administered orally to the birds. For the 10$^{th}$ to 13$^{th}$ days of age, the dosage is increased to 1 mL, while maintaining the concentration at $10^7$ CFU/mL. The control groups (T− and T+) received the same volume of sterile PBS solution. The negative control birds were treated first in order to reduce the risk of cross-contamination.

1-6/Measurements Performed on the Birds

The study ended on the 17$^{th}$ day. The performances of the birds were measured on the 0, 10$^{th}$, 14$^{th}$ and 17$^{th}$ day of the experimental period by recording the weight of the birds (in g) (FIG. 1) and the feed consumption for each cage. At the end of the test, all the birds were euthanized by asphyxia with $CO_2$. The necrotic enteritis lesions were looked for in the intestines and analyzed as described by Prescott et al. (1978, *Can. Vet. J.* 19, 181-183) (FIG. 2).

The experimental protocol is recapitulated in table 3 below. X corresponds to the day of administration of a product.

| 1-7/Statistical analysis | | | | | | | | | |
|---|---|---|---|---|---|---|---|---|---|
| Test day | 1 | 2 | 3 | 4 | 5 | 6 | 7 | 8 | 9 |
| *Lactobacillus* | X | X | | | | | | | |
| *C. perfringens* | | | | | | | | | |
| Measurements | | | | | | | | | |
| Test day | 10 | 11 | 12 | 13 | 14 | 15 | 16 | 17 | |
| *Lactobacillus* | X | X | X | X | | | | | |
| *C. perfringens* | | | | | X | X | X | | |
| Measurements | X | | | | X | | | X | |

The statistical comparisons between the different results obtained were carried out by ANOVA variance analysis using the Statgraphics® Centurion XVI software.

2/Results:

The results are presented in table 4 below.

| | Lesion score after 17 days | Weight after 17 days |
|---|---|---|
| Negative control (T−) | 0.88 $^{c}$ | 765.00 $^{a}$ |
| Positive control (T+) | 1.67 $^{ab}$ | 699.58 $^{c}$ |
| *Lb. reuteri* | 1.29 $^{bc}$ | 709.79 $^{bc}$ |
| *Lb. salivarius* | 1.50 $^{ab}$ | 707.50 $^{bc}$ |
| *Lb. reuteri + Lb. salivarius* | 1.00 $^{c}$ | 753.13 $^{ab}$ |

The index letters (a, b, c) indicate significant statistical differences. The groups which have the same letter do not differ significantly.

Figure 2:
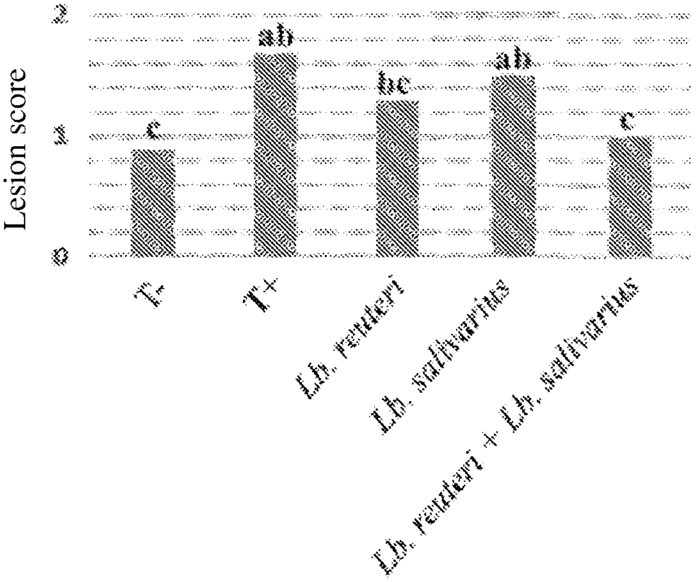
FIG. 2 represents the efficiency of the bacterial mixture according to the invention in terms of the lesion score of the chickens. The letters (a, b, c) indicate statistically significant differences.

The results of FIG. 1 show that the chickens of the group treated with *Lb. reuteri* or *Lb. salivarius* have a non-significant increase of their weights (709.79 g and 707.50 g, respectively) with respect to the positive control group (T+). This increase does not make it possible to find a weight of the chickens similar to that of the negative control group (T−).

On the contrary, the chickens of the group treated with the mixture of *Lb. reuteri* and Lb. *salivarius* have weights (753.13 g) similar to those of the group of unchallenged chickens (765 g), which are significantly different from the infected group (699.58 g).

Concerning the intestinal lesions caused by the administration of *C. perfringens* (FIG. 2), it is apparent from the data that the administration of *Lb. reuteri* or *Lb. salivarius* alone to the groups of challenged chickens does not significantly decrease the lesion score with respect to the T+ group.

A significant decrease of the intestinal lesions is obtained on the chickens of the group treated with the mixture of *Lb. reuteri* and *Lb. salivarius*, which have a lesion score (1.00) similar to that of the group of unchallenged chickens T− (0.88) and significantly different from that of the infected group T+ (1.67).

In conclusion, these in vivo data show that the supplementation with *Lb. reuteri* and *Lb. salivarius* combined produces a protective effect against necrotic enteritis in chickens.

The invention claimed is:

1. A mixture of microorganisms comprising a *Lactobacillus reuteri* strain and a *Lactobacillus salivarius* strain, wherein:

the *Lb. reuteri* strain is the strain deposited at the CNCM (Collection Nationale de Cultures de Microorganismes, Institut Pasteur, 25 rue du Docteur Roux, 75724 Paris Cedex 15) under number 1-5500 on Mar. 4, 2020; or the *Lb. salivarius* strain is the strain deposited at the CNCM under number I-5501 on Mar. 4, 2020, and/or the strain deposited at the CNCM under number 1-5502 on Mar. 4, 2020.

2. The mixture according to claim 1, wherein the microorganisms in the mixture consist of one *Lb. reuteri* strain and at least one *Lb. salivarius* strain.

3. The mixture according to claim 1, wherein the strains have an inhibitory activity on the growth and/or the activity of *Clostridium perfringens*.

4. A composition comprising the mixture according to claim 1 and at least one adjuvant, excipient, preservative, nutritional substance, or coating.

5. The composition according to claim 4 which is in lyophilized form.

6. An animal additive or feed product comprising the mixture according to claim 1.

7. A method of preventing and/or treating necrotic enteritis in an animal, the method comprising administering to the animal the mixture of claim 1.

8. The method according to claim 7, wherein the mixture is administered orally.

9. The method according to claim 7, wherein the animal is a poultry animal.

10. A strain corresponding to:

the strain deposited at the CNCM (Collection Nationale de Cultures de Microorganismes, Institut Pasteur, 25 rue du Docteur Roux, 75724 Paris Cedex 15) under number 1-5500 on Mar. 4, 2020; or the strain deposited at the CNCM (Collection Nationale de Cultures de Microorganismes, Institut Pasteur, 25 rue du Docteur Roux, 75724 Paris Cedex 15) under number 1-5501 on Mar. 4, 2020; or the strain deposited at the CNCM (Collection Nationale de Cultures de Microorganismes, Institut Pasteur, 25 rue du Docteur Roux, 75724 Paris Cedex 15) under number 1-5502 on Mar. 4, 2020.

11. The mixture according to claim 1, wherein the microorganisms in the mixture consist of one *Lb. reuteri* strain and of one *Lb. salivarius* strain.

12. The mixture according to claim 1, wherein the *Lb. salivarius* strain is the strain deposited at the CNCM under number 1-5501 or the strain deposited at the CNCM under number 1-5502.

13. The method according to claim 7, wherein the *Lb. reuteri* strain is the strain deposited at the CNCM under number 1-5500 on Mar. 4, 2020.

14. The method according to claim 7, wherein the *Lb. salivarius* strain is the strain deposited at the CNCM under number 1-5501 or the strain deposited at the CNCM under number 1-5502.

15. The method according to claim 13, wherein the *Lb. salivarius* strain is the strain deposited at the CNCM under number 1-5501 or the strain deposited at the CNCM under number 1-5502.

16. The method of claim 9, wherein the poultry animal is a chicken.

17. The mixture according to claim 1 that comprises the *Lb. reuteri* strain deposited at the CNCM under number 1-5500 and the *Lb. salivarius* strain deposited at the CNCM under number 1-5501.

18. The mixture according to claim 1 that comprises the *Lb. reuteri* strain deposited at the CNCM under number I-5500 and the *Lb. salivarius* strain deposited at the CNCM under number 1-5502.

19. The mixture according to claim 1 that comprises the *Lb. reuteri* strain deposited at the CNCM under number 1-5500, the *Lb. salivarius* strain deposited at the CNCM under number 1-5501, and the *Lb. salivarius* strain deposited at the CNCM under number 1-5502.

* * * * *